US010219988B2

(12) United States Patent
Midha et al.

(10) Patent No.: US 10,219,988 B2
(45) Date of Patent: *Mar. 5, 2019

(54) ORAL CARE COMPOSITIONS CONTAINING GEL NETWORKS AND POTASSIUM NITRATE

(71) Applicant: The Procter & Gamble Company, Cincinnati, OH (US)

(72) Inventors: Sanjeev Midha, Mason, OH (US); Lawrence Edward Dolan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,179

(22) Filed: Mar. 31, 2017

(65) Prior Publication Data

US 2017/0281483 A1    Oct. 5, 2017

Related U.S. Application Data

(60) Provisional application No. 62/317,415, filed on Apr. 1, 2016.

(51) Int. Cl.
| | | |
|---|---|---|
| *A61Q 11/00* | (2006.01) | |
| *A61K 8/21* | (2006.01) | |
| *A61K 8/02* | (2006.01) | |
| *A61K 6/00* | (2006.01) | |
| *A61K 8/19* | (2006.01) | |
| *A61K 8/22* | (2006.01) | |
| *A61K 8/25* | (2006.01) | |
| *A61K 8/34* | (2006.01) | |
| *A61K 8/24* | (2006.01) | |
| *A61K 8/46* | (2006.01) | |
| *A61K 8/04* | (2006.01) | |

(52) U.S. Cl.
CPC .............. *A61K 8/19* (2013.01); *A61K 8/0216* (2013.01); *A61K 8/042* (2013.01); *A61K 8/21* (2013.01); *A61K 8/22* (2013.01); *A61K 8/24* (2013.01); *A61K 8/25* (2013.01); *A61K 8/342* (2013.01); *A61K 8/463* (2013.01); *A61Q 11/00* (2013.01); *A61K 2800/28* (2013.01); *A61K 2800/412* (2013.01)

(58) Field of Classification Search
CPC ...... A61Q 11/00; A61K 8/21; A61K 2800/48; A61K 2800/28; A61K 2800/92; A61K 8/042

See application file for complete search history.

(56) References Cited

U.S. PATENT DOCUMENTS

| | | | |
|---|---|---|---|
| 3,551,559 A * | 12/1970 | Miles | ........................ A61K 8/02 424/49 |
| 4,666,517 A | 5/1987 | Bakar | |
| 5,093,112 A | 3/1992 | Birtwistle et al. | |
| 5,512,278 A | 4/1996 | Mundschenk | |
| 9,005,585 B2 | 4/2015 | Deckner et al. | |
| 2006/0034784 A1 | 2/2006 | Cahen et al. | |
| 2006/0210491 A1 | 9/2006 | Behan et al. | |
| 2008/0081023 A1 * | 4/2008 | Deckner | ................. A61K 8/042 424/49 |
| 2014/0127145 A1 * | 5/2014 | Deckner | ............... A61K 8/0241 424/57 |
| 2014/0308322 A1 | 10/2014 | Midha et al. | |
| 2015/0023890 A1 | 1/2015 | Joziak et al. | |

FOREIGN PATENT DOCUMENTS

| | | |
|---|---|---|
| AU | 2002318865 A1 | 6/2004 |
| EP | 0348560 A1 | 1/1990 |
| WO | WO2007136381 A1 | 11/2007 |
| WO | WO2008042279 A2 | 4/2008 |
| WO | WO2011053877 A2 | 5/2011 |

OTHER PUBLICATIONS

U.S. Appl. No. 15/475,172, filed Mar. 31, 2017, Sanjeev Midha et al.
U.S. Appl. No. 15/475,169, filed Mar. 31, 2017, Sanjeev Midha et al.
U.S. Appl. No. 15/475,170, filed Mar. 31, 2017, Sanjeev Midha et al.
U.S. Appl. No. 15/475,168, filed Mar. 31, 2017, Hoke et al.
International Search Report and Written Opinion for PCT/US2017/025234 dated Jun. 20, 2017.

* cited by examiner

*Primary Examiner* — Tracy Liu

(74) *Attorney, Agent, or Firm* — Parker D. McCrary; Alexandra S. Anoff

(57) ABSTRACT

An oral care composition containing a gel network phase, potassium nitrate, an abrasive and a fluoride ion source. The gel network phase contains a fatty amphiphile and a secondary surfactant. The oral care composition contains at least about 12% fatty amphiphile and phase separation is not visually perceptible.

9 Claims, 3 Drawing Sheets

ORAL CARE COMPOSITIONS CONTAINING GEL NETWORKS AND POTASSIUM NITRATE

FIELD OF THE INVENTION

The present invention relates to an oral care composition. More particularly a toothpaste composition containing a gel network and potassium nitrate.

BACKGROUND OF THE INVENTION

Oral care compositions, including toothpaste compositions, can contain fluoride salts, abrasives, and flavors to clean teeth, freshen breath, and maintain the aesthetics and health of the oral cavity, including the teeth and gums. It can also be desirable to include potassium nitrate ($KNO_3$) in oral care compositions to help reduce pain from sensitive teeth (dentinal hypersensitivity).

Formulating toothpaste compositions with the proper rheology can be very challenging. The composition must not be too thick so it can easily dispense out of a tube but thick enough to stand up on a toothbrush without sinking into the bristles. The viscosity of the oral composition must remain stable over time as not to continue to thicken so the oral composition remains easy to dispense during the shelf life. Once dispensed from a container, the oral composition should not be stringy or sticky as to be messy for a consumer to use. The oral composition must also easily disperse once in the mouth and foam. It is also desired that the oral composition not stick to a sink or leave difficult to remove residue. In addition to balancing the viscosity and shear thinning to formulate acceptable rheology, the oral composition must also keep active ingredients including fluoride salts and potassium nitrate stable and available.

One way to improve toothpaste rheology and stability is to include a gel network phase as a structurant. The gel network phase can include a fatty amphiphile, such as a fatty alcohol, and a secondary surfactant. Including a gel network phase can also provide a unique brushing experience. For instance, toothpaste that contains a gel network phase can have excellent foaming and the foam may not easily break down during brushing, even when it is used with an electric toothbrush. Also, some commercially available toothpastes can feel harsh and can irritate a user's mouth, however, toothpastes containing gel networks can feel smooth and are generally non-irritating. Additionally, after brushing, the mouth not only feels fresh and clean, but a user's teeth can feel especially smooth and the smoothness can persist throughout the day because the amount of biofilm that builds on the teeth between brushings can be significantly reduced.

However, it can be particularly difficult to formulate stable toothpaste compositions with a gel network phase that also contains an effective level of a salt, such as $KNO_3$. For instance, unacceptable phase separation has been observed in toothpastes that contain a gel network phase and $KNO_3$.

As such, there is a need for an improved oral care composition that has an effective level of a salt, such as $KNO_3$, and sufficient rheology and where the phases are stable.

SUMMARY OF THE INVENTION

An oral care composition comprising: (a) a gel network phase comprising at least about 14% fatty amphiphile fatty amphiphile and a secondary surfactant; (b) from about 1% to about 8%, by weight of the composition, potassium nitrate; (c) from about 2% to about 25%, by weight of the composition, abrasive wherein the abrasive comprises precipitated silica; and (d) a fluoride ion source selected from the group consisting of stannous fluoride, sodium fluoride, potassium fluoride, amine fluoride, sodium monofluorophosphate, indium fluoride, amine fluoride, and combinations thereof; wherein the fluoride ion source provides a fluoride ion concentration from about 0.005% to about 2.0%, by weight of the composition; and wherein phase separation is not visually perceptible as determined by the phase separation method.

An oral care composition comprising: (a) a gel network phase comprising from about 14% to about 20%, by weight of the composition, fatty amphiphile and a secondary surfactant; (b) from about 1% to about 8%, by weight of the composition, potassium nitrate; (c) from about 2% to about 25%, by weight of the composition, abrasive; (d) a fluoride ion source selected from the group consisting of stannous fluoride, sodium fluoride, potassium fluoride, amine fluoride, sodium monofluorophosphate, indium fluoride, amine fluoride, and combinations thereof; wherein the fluoride ion source provides a fluoride ion concentration from about 0.005% to about 2.0%, by weight of the composition; wherein phase separation is not visually perceptible as determined by the phase separation method.

A method for making an oral care composition comprising the steps of: (a) combining water and a fatty amphiphile; (b) heating the water and the fatty amphiphile until the fatty amphiphile melts and a solution is formed; (c) cooling the solution; (d) adding a fluoride ion source and/or an abrasive and/or a peroxide; (e) adding a secondary surfactant; (f) mixing until the composition is substantially homogeneous; (g) deaerating until the composition is substantially free of air; wherein a gel network is formed.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
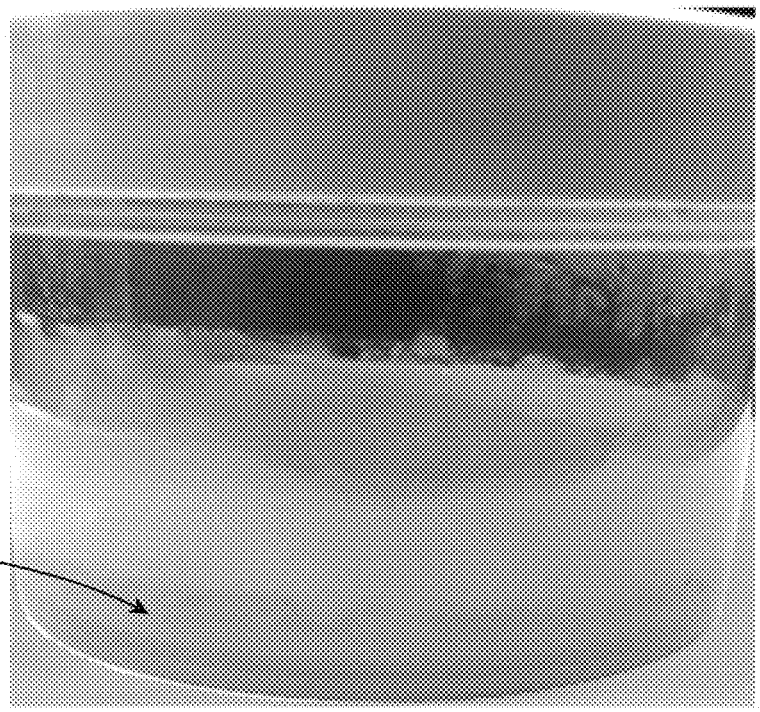
FIG. 1 is a digital photograph of Example 1.

Oral care compositions can include fluoride, peroxide, potassium nitrate, abrasives, flavors, and other ingredients to provide benefits like reducing plaque and tartar, reducing pain from sensitive teeth, preventing cavities, preventing and reversing gingivitis, building protection against sensitivity, freshening bad breath, and whitening teeth.

Some consumers are particularly interested in a product that contains potassium nitrate ($KNO_3$) to help alleviate dentinal hypersensitivity. It can be particularly desirable to include potassium nitrate in a toothpaste formulation that includes a structurant that includes a gel network phase, which can provide improved rheology and stability and a unique brushing experience. During brushing, the gel network can help the toothpaste feel smooth and non-irritating and can also provide excellent foaming throughout brushing. Furthermore, after brushing teeth can feel especially smooth and the amount of biofilm that accumulates on a user's teeth between brushings can be significantly reduced.

However, it can be difficult to formulate a stable toothpaste composition that contains both a gel network phase and an effective level of a salt, such as $KNO_3$. It has been observed that toothpastes containing a gel network phase and $KNO_3$ can separate into phases, where the water phase separates from the gel/paste phase, which is unacceptable. While not wishing to be bound by theory, it is hypothesized that the salt interrupts the structure of the gel network, which results in the phase separation. Phase separation in toothpaste is particularly problematic, as toothpaste is generally dispensed from a narrow tube with a small opening, which makes it very difficult for a consumer to stir or otherwise mix the toothpaste to reincorporate the separated phase.

Therefore, it can be desirable to improve the toothpaste composition so it can include a salt, such as $KNO_3$ and a gel network phase and be phase stable. The amount of fatty amphilphile and/or the amount of secondary surfactant can be increased to improve phase stability. For instance, the oral care composition can contain a gel network phase containing a fatty alcohol and a surfactant, fluoride specifically sodium fluoride or stannous fluoride, potassium nitrate, and an abrasive, specifically a precipitated silica abrasive. The composition can contain at least about 14% fatty alcohol. The composition can contain another salt, for instance pyrophosphates, which can help control tartar, in addition to or instead of potassium nitrate.

The toothpaste composition can be phase stable and phase separation is not visually perceptible, as determined by the Phase Separation Method, described hereafter.

The composition may not have a visually perceptible phase separation. The term "visually perceptible" as used herein means that a human viewer can visually discern a phase separation with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of approximately 18 inches.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The composition can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the articles "a" and "an" are understood to mean one or more of the material that is claimed or described, for example, "an abrasive" or "a surfactant".

As used herein, the word "or" when used as a connector of two or more elements is meant to include the elements individually and in combination; for example X or Y, means X or Y or both.

The term "dispenser", as used herein, means any pump, tube, or container suitable for dispensing compositions such as toothpastes.

The term "effective amount or "effective level" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%. An "effective level" of potassium nitrate can be about 5%.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Oral care compositions can include toothpaste, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "teeth", as used herein, refers to natural teeth as well as artificial teeth or dental prosthesis.

The term "toothpaste", as used herein, includes tooth or subgingival paste, gel, or liquid formulations unless otherwise specified. The toothpaste composition may be a single phase composition or may be a combination of two or more separate toothpaste compositions. The toothpaste composition may be in any desired form, such as deep striped, surface striped, multilayered, having a gel surrounding a paste, or any combination thereof. Each toothpaste composition in a toothpaste comprising two or more separate toothpaste compositions may be contained in a physically separated compartment of a dispenser and dispensed side-by-side. As Herein, the terms "toothpaste" and "dentifrice" can be used interchangeably.

The term "secondary surfactant" as used herein means a surfactant other than a fatty amphiphile. Various types of suitable surfactants are listed below. There may be more than one secondary surfactants. There can be at least one secondary surfactant in the gel network phase and there may be another surfactant in the oral carrier phase.

The term "water", as used herein, refers to deionized water, unless otherwise specified.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

Dentifrice compositions containing $KNO_3$ and a gel network phase containing a fatty amphiphile and a secondary surfactant can be made. FIGS. 1 to 6 show digital photographs of Examples 1-6, as described hereafter. Examples 1 to 6 have varying amounts of fatty amphiphile and varying levels and types of abrasives. Examples 1 and 2 have the lowest amount of fatty amphiphile and Example 6 has the highest amount of fatty amphiphile. All of the examples contain Lanette® W, a commercially available mixture of fatty alcohols and a secondary surfactant and the mixture is approximately 45% cetyl alcohol, 45% stearyl alcohol, and 10% sodium lauryl sulfate (available from BASF, Florham Park, N.J.). Each example was made, as described hereafter, and phase separation was determined by the Phase Separation Method, as described hereafter. A summary of Examples 1-6 is in the table below:

|  | Ex. 1 (wt. %) | Ex. 2 (wt. %) | Ex. 3 (wt. %) | Ex. 4 (wt. %) | Ex. 5 (wt. %) | Ex. 6 (wt. %) |
| --- | --- | --- | --- | --- | --- | --- |
| Lanette ® W | 11.11 | 11.11 | 14.44 | 15.56 | 16.05 | 17.78 |
| wt. % fatty amphiphile | 10.00 | 10.00 | 13.00 | 14.00 | 14.45 | 16.00 |
| wt. % surfactant | 1.11 | 1.11 | 1.44 | 1.56 | 1.60 | 1.78 |
| Potassium Nitrate USP | 5.00 | 5.00 | 5.00 | 5.00 | 5.56 | 5.00 |
| Zeodent ® 109 | — | 7.50 | — | — | — | — |
| Tospearl ® 145 | 10.00 | — | 10.00 | — | — | — |
| Zeodent ® 119 | — | — | — | 15.00 | — | 15.00 |
| Sodium Lauryl Sulfate Solution[1] | 20.00 | 17.86 | 17.86 | 20.00 | 19.84 | 17.85 |
| wt. % SLS | 5.80 | 5.18 | 5.18 | 5.80 | 5.75 | 5.18 |
| wt. % water | 14.20 | 12.68 | 12.68 | 14.20 | 14.09 | 12.68 |

[1]Sodium Lauryl Sulfate (SLS) Solution contains 29% SLS

Example 1 contains 11.11% Lanette® W (10% fatty amphiphile), 5% potassium nitrate, and 10.00% Tospearl® 145. Tospearl® 145 (available from Momentive™ Performance Materials, New York, USA) are polyorganosilsequioxane particles, more specifically polymethyl organosiloxane silicone resin particles, which can be incorporated into oral care products and used as an abrasive. As shown in FIG. 1, there is visually perceptible phase separation in Example 1 as determined by the Phase Separation Method and therefore Example 1 may not be acceptable from a phase stability standpoint. While not willing to be bound by theory, it may not be desirable to use polymethyl organosiloxane particles as the abrasive. The surface of polymethyl organosiloxane particles have methyl groups and therefore the surface contains all organic moieties that makes it hydrophobic. Thus, the particles do not absorb very much of the water that is expelled from the solid phase of the formulation and the polymethyl organosiloxane particles do not help with phase stability. However, it can be desirable to include polymethyl organosiloxane particles, since they can provide other advantages to the formulation, including chemical stability.

Figure 2:
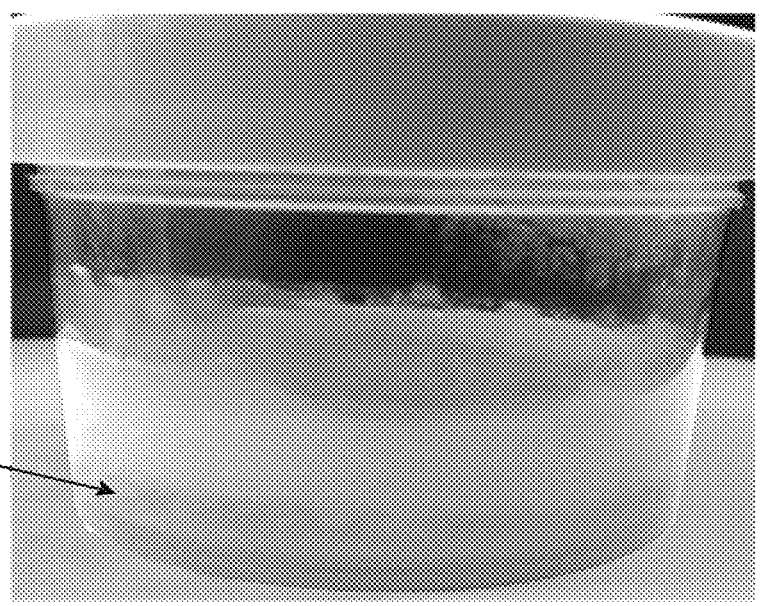
FIG. 2 is a digital photograph of Example 2.

Example 2 contains 11.11% Lanette® W (10% fatty amphiphile), 5% potassium nitrate, and 7.50% Zeodent® 109. Zeodent® 109 is a silica dental composition that can be used as an abrasive in toothpastes. It was hypothesized that a precipitated silica abrasive, such as Zeodent® 109 or Zeodent® 119, would absorb some of the water and help with phase stability. Zeodent® 109 has a BET surface area from about 19-35 $m^2/g$. BET surface area is determined by BET nitrogen absorption method of Brunaur et al., J. Am. Chem. Soc., 60, 309 (1938). See also U.S. Pat. No. 7,255,852 to Gallis. However, as shown in FIG. 2, there is visually perceptible phase separation in Example 2 as determined by the Phase Separation Method and therefore Example 2 may not be acceptable from a phase stability standpoint.

Figure 3:
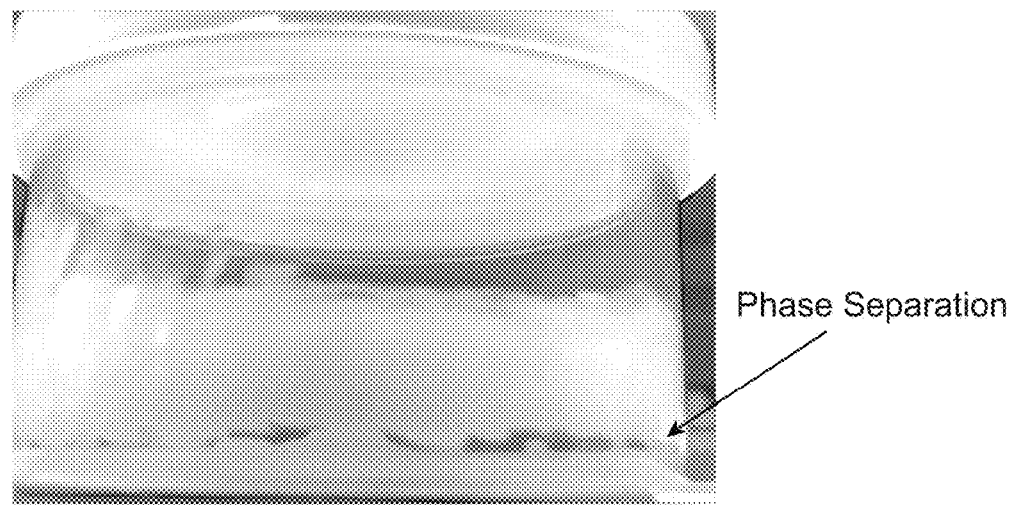
FIG. 3 is a digital photograph of Example 3.

Example 3 contains 14.44% Lanette® W (13% fatty amphiphile), 5% potassium nitrate, and 10.00% Tospearl® 145. As shown in FIG. 3, there is visually perceptible phase separation in Example 3 as determined by the Phase Separation Method and therefore Example 3 may not be acceptable from a phase stability standpoint.

Figure 4:
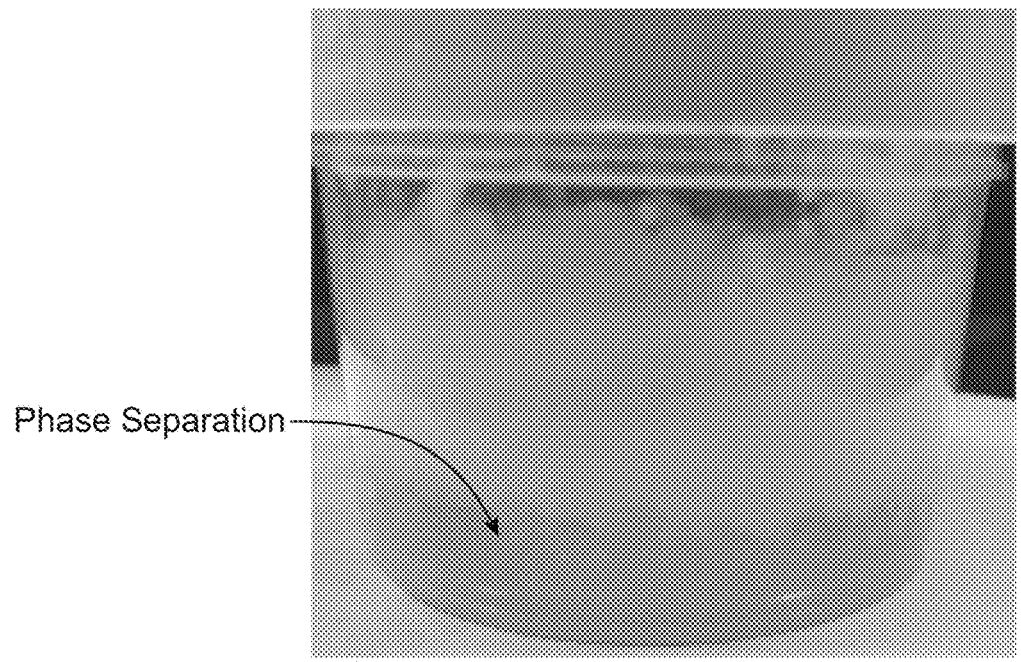
FIG. 4 is a digital photograph of Example 4.

Example 4 contains 15.56% Lanette® W (14% fatty amphiphile), 5% potassium nitrate, and 15% Zeodent® 119. Zeodent® 119 is an amorphous silica gel that can be used as an abrasive in toothpastes. Zeodent® 119 has a BET surface area of about 19-55 $m^2/g$. As shown in FIG. 4, there is visually perceptible phase separation in Example 4 as determined by the Phase Separation Method and therefore Example 4 may not be acceptable from a phase stability standpoint.

Figure 5:
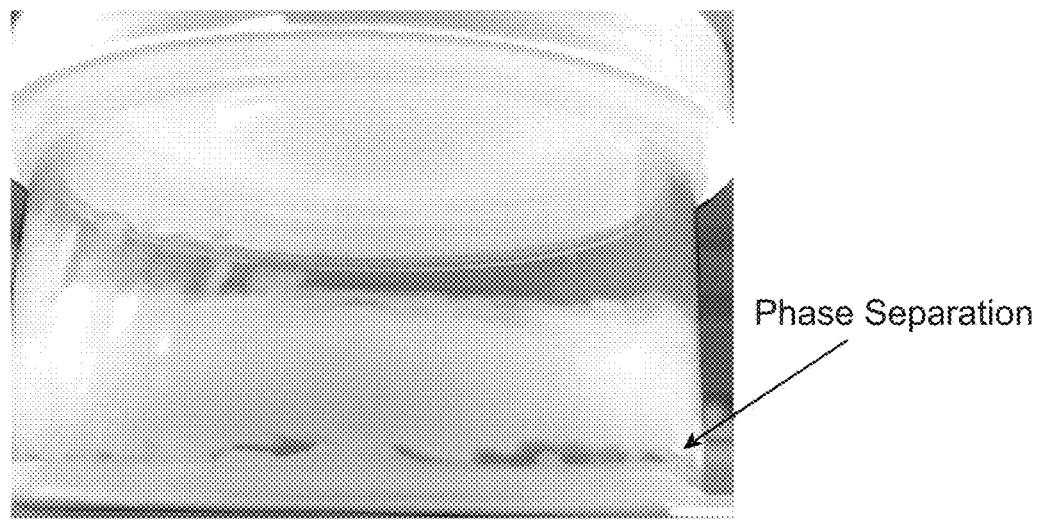
FIG. 5 is a digital photograph of Example 5.

Example 5 contains 16.05% Lanette® W (14.45% fatty amphiphile), and 5.56% potassium nitrate. Example 5 does not contain an abrasive. As shown in FIG. 5, there is visually perceptible phase separation in Example 5 as determined by the Phase Separation Method and therefore Example 5 may not be acceptable from a phase stability standpoint.

Figure 6:
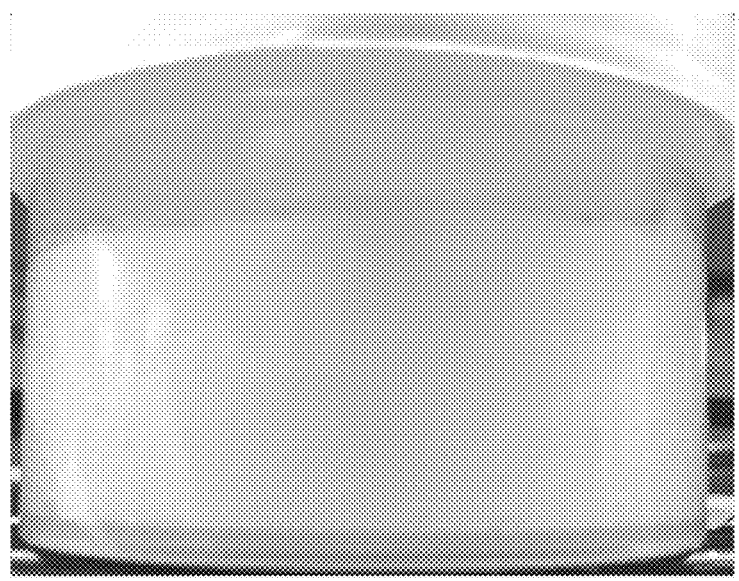
FIG. 6 is a digital photograph of Example 6.

Example 6 contains 17.78% Lanette® W (16% fatty amphiphile), 5% potassium nitrate, and 15% Zeodent® 119. As shown in FIG. 6, there is no visually perceptible phase separation in Example 6 as determined by the Phase Separation Method and therefore Example 6 may be acceptable from a phase stability standpoint.

Toothpastes that contain both gel networks and $KNO_3$ can be enjoyed by consumers. They are used the same way as regular toothpaste. For instance, the American Dental Association recommends brushing at least twice a day for two minutes with a soft-bristled brush. Then the brush is placed in a user's mouth at a 45-degree angle to the gums and gently moved back and forth in short (tooth-wide) strokes. The outer surfaces, inner surfaces, and the chewing surfaces of the teeth can be brushed. A user can also brush her tongue to remove bacteria and keep her breath fresh. The toothpaste containing gel networks can be combined with other oral care regiments such as flossing, mouthwashes, whitening regimens, and regular visits to the dentist for professional cleanings and oral exams.

The user can dispense the toothpaste from the container, which can be a metal or plastic tube. When dispensed, the first thing that a consumer may notice is the rheology of the toothpaste containing a gel network. The toothpaste can easily dispense from the container. The toothpaste can dispense cleanly out of the container onto the brush without being stringy. The nurdle can be smooth, not lumpy, and is thick enough that it stands up on the brush without sinking into the bristles.

Next, the consumer will brush her teeth. She may find that the toothpaste feels especially smooth in her mouth and the toothpaste is not irritating. Again, she may notice that the toothpaste is not stringy, but it is easily spread throughout her entire mouth. The user may notice that the toothpaste foams. The foaming can feel unique, as it builds and/or is maintained during brushing, which can last two minutes (as recommended by the American Dental Association®) or longer. The foam is not dense and heavy, like some products that may overwhelm the user. Furthermore, users may notice that foam from some current commercially available toothpastes breaks down and becomes thin and watery and causes a mess during brushing, especially if the user is brushing with an electric toothbrush. However, in toothpaste that contains a gel network phase, the foam can gently build during brushing and be very pleasant. Users may also notice that the flavor pleasantly builds intensity during brushing. After expectorating the toothpaste containing a gel network, the user may find it easily removed from the sink, for instance the toothpaste can be removed by simply turning on the water for the sink. The toothpaste containing gel networks may not stain the sink or countertop or the user's mouth or lips.

Consumers may find that these desirable properties are maintained or substantially maintained for the entire shelf life of the product. The oral care composition may not significantly thicken during the shelf life. The actives, including the fluoride component and the $KNO_3$, can be relatively stable and present at effective levels at the end of the shelf life. The toothpaste can also keep the actives available so they can deliver a therapeutic effect while brushing.

After use, a consumer may find that her teeth feel especially smooth and she may notice that this smoothness lasts for hours or even throughout the entire time between brushing. It may be determined that less biofilm forms over her teeth between brushing and consequently and therefore users of this product may have less plaque buildup over time. After using the toothpaste containing gel networks for some time (even a short period of time, such as a few brushings), a user may find that her gums are less sensitive and may have reduced bleeding. A user may also have more pleasant dental checkups because less plaque needs to be removed and her gums are not as sensitive. The user may believe that her teeth look especially white as well and/or the teeth may actually be whiter from removal of surface stains and/or intrinsic whitening. The user may have a fresh clean feeling in her mouth for an extended period of time. The user may have fresh breath for an extended period of time. The user may notice that her teeth are less sensitive.

The toothpaste composition can have a shelf life of at least about 1 year, at least about 1.5 years, at least about 2 years, at least about 2.5 years, and/or at least about 3 years.

As used herein, "fatty amphiphile" refers to a compound having a hydrophobic tail group and a hydrophilic head group which does not make the compound water soluble (immiscible), wherein the compound also has a net neutral charge at the pH of the oral composition. The fatty amphiphile can be selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, phospholipids, and combinations thereof. Suitable fatty amphiphiles include a combination of cetyl alcohol and stearyl alcohol. The fatty amphiphile can be a fatty alcohol.

The oral care compositions may contain a fatty amphiphile in an amount greater than about 10%, greater than about 11%, greater than about 13%, greater than about 14%, greater from about 14.5%, greater than about 15%, greater than about 15.5%, and/or greater than about 16%. The oral care composition may contain a fatty amphiphile in an amount less than about 40%, less than about 35%, less than about 30%, less than about 25%, less than about 22%, less than about 20%, less than about 19%, less than about 18%, and/or less than about 17%. The oral care composition may contain a fatty amphiphile in an amount from about 3% to about 30%, from about 4% to about 28%, from about 5% to about 26%, from about 7% to about 25%, from about 8% to about 23%, from about 10% to about 21%, from about 12% to about 20%, from about 13% to about 19%, from about 14% to about 18%, from about 15% to about 17%, and/or about 16%.

The oral care composition can contain one or more secondary surfactants. The secondary surfactant is typically water soluble or miscible in the solvent or oral carrier. Suitable secondary surfactants include anionic, zwitterionic, amphoteric, cationic, and nonionic secondary surfactants. Anionic secondary surfactants such as sodium lauryl sulfate, are used. The composition can contain from about 1% to about 15% anionic secondary surfactant, from about 2% to about 10%, from about 3% to about 8.5%, from about 4% to about 8%, from 5% to about 7.5%, and/or from about 6% to about 7%. The secondary surfactants may be a combination of more than one type of secondary surfactants, such as an anionic and nonionic secondary surfactant. Suitable solvents for the present invention can include water, edible polyhydric alcohols such as glycerin, diglycerin, triglycerin, sorbitol, xylitol, butylene glycol, erythritol, polyethylene glycol, propylene glycol, and combinations thereof.

Secondary surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds can include mono-, di- or triesters represented by the general structure below wherein Z1, Z2, or Z3 may be identical or different, at least one being an organic moiety, in one example selected from linear or branched, alkyl or alkenyl group of from 1 to 22 carbon atoms, optionally substituted by one or more phosphate groups; alkoxylated alkyl or alkenyl, (poly)saccharide, polyol or polyether group.

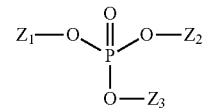

Some other organophosphate agents include alkyl or alkenyl phosphate esters represented by the following structure:

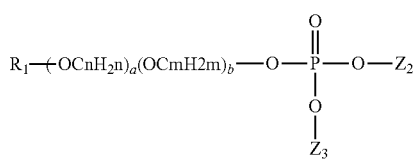

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b-group. Examples of suitable agents include alkyl and alkyl (poly)alkoxy phosphates such as lauryl phosphate; PPGS ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. The alkyl phosphate can be polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric secondary surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric secondary surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these secondary surfactants are soapy, bitter, chemical, or artificial. The composition can contain from about 0.1% to about 6% amphoteric secondary surfactant, from about 0.5% to about 4%, from about 0.75% to about 2%, and/or from about 1% to about 1.5%.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic secondary surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic secondary surfactants can also act as germicides in the oral care compositions disclosed herein.

The oral care composition can have a viscosity from about 5 BKUs to about 70 BKUs, from about 10 BKUs to about 45 BKUs, from about 12 BKUs to about 40 BKUs from about 15 BKUs to about 35 BKUs, from about 18 BKUs to about 30 BKUs, from about 20 BKUs to about 28 BKUs, and/or from about 22 BKUs to about 25 BKUs. The oral care compositions can have a viscosity from about 10 BKUs to about 200 BKUs, from about 20 BKUs to about 175 BKUs from about 30 BKUs to about 150 BKUs, and/or from about 50 BKUs to 100 BKUs. Viscosity can measured by the Brookfield Viscosity Test as described hereafter.

The oral care composition can have a shelf life, when stored below 40° C., of at least 6 months, at least 1 year, at least 18 months, at least 2 years, at least 30 months, and/or in at least 3 years. The shelf life can be from about 6 months to about 5 years, from about 1 year to about 3 years, and/or from about 1.5 years to about 2.5 years.

The oral care composition can have a pH from about 2 to about 10, from about 4 to about 9, from about 5 to about 8, and/or from about 6 to about 7.5. pH can be measured using the pH Test Method as described hereafter.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

It is common to have a fluoride compound present in toothpastes and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 to Briner et al. and U.S. Pat. No. 3,678,154 to Widder et al.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 6%, by total weight of the oral care composition. Some metal salts which may be used in the present invention, such as zinc chloride, zinc citrate, copper gluconate, and zinc gluconate, are also associated with an off taste described as dirty, dry, earthy, metallic, sour, bitter, and astringent.

Stannous salts include stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients used to stabilize the stannous may be included, such as the ingredients described in Majeti et al. and Prencipe et al.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof. The composition can contain from about 0.05% to about 15% potassium nitrate, from about 0.5% to about 10%, from about 1% to about 8%, from about 2% to about 7%, from about 3% to about 6%, and from about 4% to about 5.5%, by total weight of the oral care composition.

The copper salt can be selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. The copper salt can be selected from copper gluconate, copper acetate, copper glycinate, and combinations thereof.

Sweeteners can include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, Minn., which is an extract from the leaves of the *Stevia rebaudiana* plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable examples of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials can include water, glycerin, sorbitol, polyethylene glycols including those having a molecular weight of less than about 50,000, propylene glycol and other edible polyhydric alcohols, ethanol, or combinations thereof. The oral care compositions of the present invention can include from about 5% to about 80%, by weight of the composition, of a carrier material. The compositions can contain carrier materials in an amount of from about 10% to about 40%, by total weight of the oral care composition.

The composition can contain from about 15% to about 95% water, from about 20% to about 85%, from about 25% to about 70%, from about 28% to about 60%, from about 30% to about 50%, from about 31% to about 48%, from about 32% to about 45%, and/or from about 33% to about 43%. The composition can contain from about 1% to about 20% water, from about 2% to about 15% water, from about 3% to about 10% water, and/or from about 4% to about 8% water. The composition can contain greater than about 5% water, greater than about 8%, greater than about 10%, greater than about 15%, greater than about 20%, greater than about 25%, greater than about 30%, greater than about 40%, and/or greater than about 50%.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium] alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, and flavor oils such as thymol. The antimicrobial agent can include triclosan.

The compositions of the present invention may contain antimicrobial agents in an amount of from about 0.035% or more, from about 0.1% to about 2.0%, from about 0.045% to about 1.0%, or from about 0.05% to about 0.10%, by total weight of the oral care composition. The compositions may contain from about 0.001% to about 1.5% antimicrobial agent, from about 0.005% to about 0.8%, from about 0.01% to about 0.7%, from about 0.05% to about 0.5%, and/or from about 0.1% to about 0.3%.

Non-limiting examples of peroxide (peroxygen) compounds can include hydrogen peroxide, urea peroxide, calcium peroxide, sodium peroxide, zinc peroxide, polyvinylpyrrolidone peroxide complex or combinations thereof. The composition can contain greater than about 0.05% peroxide, greater than about 0.75%, greater than about 1%, greater than about 1.25%, greater than about 1.5%, greater than about 1.75%. greater than about 2%, greater than about 2.25%, greater than about 2.5%, greater than about 2.75%, greater than about 2.85%, greater than about 2.9%, greater than about 2.95%, greater than about 3%, greater than about 4%, greater than about 5%, and/or greater than about 6%. The composition can contain from about 0.01% to 10% peroxide, from about 0.05% to about 8%, from about 0.1% to about 5%, from about 0.5% to about 4.5%, from about 1% to about 4%, from about 1.5% to about 3.5%, and/or from about 2% to about 3%. The composition can contain from about 1% to about 10% peroxide, from about 2% to about 8% peroxide, from about 3% to about 7% peroxide, and/or from about 4% to about 6% peroxide. The composition can contain from about 0.01% to about 6% peroxide, from about 0.05% to about 3%, and/or from about 0.1% to about 1%.

The composition can be free of or substantially free of a peroxide component.

The oral care composition can include bleaching agents. Bleaching agents can include perborates, percarbonates, peroxyacids, persulfates, peracids, peracid precursor systems, and preformed peracids and combinations thereof. One example of a percarbonate is sodium percarbonate. An example of a persulfate includes oxones.

The compositions of the present invention may contain bleaching agents in an amount of from about 0.01% to about 30%, from about 0.1% to about 10%, or from about 0.5% to about 5%, by total weight of the oral care composition.

Flavors that may be used in oral care compositions are mint oils, and components thereof, wintergreen, clove bud oil, cassia, sage, parsley oil, marjoram, lemon, orange, propenyl guaethol, heliotropine, cis-4-heptenal, diacetyl, methyl-ρ-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, isopulegol, piperitone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors can be present in an amount of from about 0.4% to about 5%, by total weight of the oral care composition, from about 0.8% to about 4%, from about 1% to about 3.5%, and/or from about 1.5% to about 3%. It can be desirable to have a flavor composition at less than about 4%, less than about 3.5%, by total weight of the oral care composition, less than about 3%, and/or less than about 2%.

Dentifrice compositions of the present invention may also comprise an anti-calculus agent, which may be present from about 0.05% to about 50%, by weight of the dentifrice composition, in another embodiment is from about 0.05% to about 25%, and in another embodiment is from about 0.1% to about 15%. The compositions can contain an amount of anti-calculus agent that is effective in tartar control. The amount of pyrophosphate salt may be from about 1.5% to about 15%, from about 2% to about 10%, or from about 3% to about 8%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. The composition can contain from about 1% to about 30% polyphosphate salts, from about 5% to about 25%, from about 10% to about 20%, from about 11% to about 15%, and/or about 13%. Polyphosphates larger than tetrapolyphosphate usually occur as amorphous glassy materials. In one embodiment the polyphosphates are those manufactured by FMC Corporation, which are commercially known as Sodaphos(n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Colorants that may be used in oral care compositions include D&C Yellow No. 10, FD&C Blue No. 1, FD&C Red No. 40, D&C Red No. 33 and combinations thereof. The composition can contain colorant in an amount of from about 0.0001% to about 0.1% or from about 0.001% to about 0.01%, by weight of the oral care composition. Some colorants provide an unwanted taste, for instance, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 2%, by weight of the oral care composition. The most well-known cooling sensate compound can be menthol, particularly L-menthol, which is found naturally in peppermint and spearmint oils notably of *Mentha piperita*, *Mentha arvensis* L and *Mentha viridis* L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For instance, d-neomenthol is reported to have a cooling threshold of about 25,000 ppb and 1-neomenthol about 3,000 ppb.

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the p-menthanecarboxamide compounds such as N-ethyl-p-menthan-3-carboxamide, known commercially as "WS-3", and others in the series such as WS-5 (N-ethoxycarbonylmethyl-p-menthan-3-carboxamide), WS-12 (1R*,2S*)-N-(4-Methoxyphenyl)-5-methyl-2-(1-methylethyl)cyclohexanecarboxamide] and WS-14 (N-tert-butyl-p-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and p-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted p-menthane carboxamides are described in WO 2005/049553A1 including N-(4-cyanomethylphenyl)-p-menthanecarboxamide, N-(4-sulfamoylphenyl)-p-menthanecarboxamide, N-(4-cyanophenyl)p-menthanecarboxamide, N-(4-acetylphenyl)-p-menthanecarboxamide, N-(4-hydroxymethylphenyl)-p-menthanecarboxamide and N-(3-hydroxy-4-methoxyphenyl)-p-menthanecarboxamide. Other N-substituted p-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917,613; 3,991,178; 5,703,123; 5,725,865; 5,843,466; 6,365,215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630 and phosphine oxides as reported in U.S. Pat. No. 4,070,496.

Warming sensates can include ethanol; *capsicum*; nicotinate esters, such as benzyl nicotinate; polyhydric alcohols; *capsicum* powder; a *capsicum* tincture; *capsicum* extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

The abrasive polishing material has a BET surface area greater than about 5 $m^2/g$, greater than about 10 $m^2/g$, greater than about 15 $m^2/g$, greater than about 18 $m^2/g$, greater than about 25 $m^2/g$, greater than about 30 $m^2/g$, greater than about 35 $m^2/g$, greater than about 40 $m^2/g$, and/or greater than about 50 $m^2/g$. The BET surface area of the abrasive polishing material can be from about 5 $m^2/g$ to about 30 $m^2/g$, from about 10 $m^2/g$ to about 200 $m^2/g$, from about 20 $m^2/g$ to about 150 $m^2/g$, from about 25 $m^2/g$ to about 100 $m^2/g$, from about 30 $m^2/g$ to about 75 $m^2/g$, from about 35 $m^2/g$ to about 60 $m^2/g$, from about 38 $m^2/g$ to about 50 $m^2/g$, and/or from about 40 $m^2/g$ to about 45 $m^2/g$. The precipitated silica can have a BET surface area from about 19 $m^2/g$ to about 55 $m^2/g$ and/or from about 19 $m^2/g$ to about 35 $m^2/g$. The silica can have a BET surface area from about 10 $m^2/g$ to about 80 $m^2/g$, from about 20 $m^2/g$ to about 70 $m^2/g$, from about 25 $m^2/g$ to about 50 $m^2/g$, and/or from about 30 $m^2/g$ to about 45 $m^2/g$. BET surface area is determined by BET nitrogen absorption method of Brunaur et al., *J. Am. Chem. Soc.*, 60, 309 (1938). See also U.S. Pat. No. 7,255,852 to Gallis.

The abrasive polishing material has a LOD of about 1% to about 10%, from about 3% to about 7%, from about 4% to about 6.75%, and/or from about 5.6% to about 6.1%. The LOD can be less than about 7%, less than about 6.5%, and/or less than about 6.25%. The abrasive polishing material can have an LOI from about 2% to about 10%, from about 3% to about 7%, from about 4% to about 6%, and/or about 5.1%. The LOI can be greater than about 3%, greater than about 4%, and/or greater than about 5%. The sum of LOD and LOI can be from about 5% to about 20%, from about 7% to about 17%, from about 8% to about 15%, from about 9% to about 14%, and/or from about 10% to about 12.5%. Silicas with less than about 5% bound and free water may be considered substantially non-hydrated. The total bound and free water can be calculated by totaling two measurements, loss on drying (LOD) and loss on ignition (LOI). For loss on drying, performed first, a sample may be dried at 105° C. for two hours, the weight loss being the free water. For loss on ignition, the dried sample then may be heated for one hour at 1000° C., the weight loss being the bound water. The sum of the LOD and LOI represents the total bound and free water in the original sample.

Typical abrasive polishing materials can include silicas including gels and precipitates; aluminas; phosphates including orthophosphates, polymetaphosphates, and pyrophosphates; and mixtures thereof. Specific examples include silicone microspheres such as polyorganosilsesquioxane particles, dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. If the oral composition or particular phase comprises a polyphosphate having an average chain length of about 4 or more, calcium containing abrasives and alumina may not be preferred abrasives. The composition can be free of or substantially free of silica.

The composition can contain a silica abrasive. Silica abrasive polishing materials that may be used in the present invention, as well as other abrasives, generally have an average particle size ranging between about 0.1 to about 30 μm or from about 5 to about 15 μm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. Nos. 4,340,583; 5,589,160; 5,603,920; 5,651,958; 5,658,553; and 5,716,601.

The abrasive can include polymethyl organosiloxane particles. The types of polymethyl organosiloxane particles useful in the oral care compositions of the present invention are described in more detail in U.S. Pat. No. 9,017,647. It may be advantageous to select an abrasive containing polymethyl organosiloxane particles because they are less reactive with ingredients commonly found in oral care compositions, in including oral care actives.

The abrasive can include calcium pyrophosphate. The abrasive can include poly(methyl methacrylate), calcium carbonate, dicalcium phosphate, and/or barium sulfate.

The composition can include from about 2% to about 35%, by weight, abrasive, from about 5% to about 30%, from about 7% to about 25%, from about 9% to about 20%, from 10% to 18%, from 12% to 17%, and/or from about 13% to about 16%.

Thickening material or binders may be used to provide a desirable consistency to the oral care compositions of the present invention.

Thickening materials can include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. The thickening material can be carrageenan. Thickening materials can be used in an amount from about 0.1% to about 15%, by weight of the oral care composition. Thickening materials can be used in an amount from about 0.01% to about 3%, from about 0.1% to about 2%, from about 0.2% to about 1 from about 0.25% to about 0.75%, from about 0.27% to about 0.5%, and from about 0.3% to about 0.4%. The oral care compositions can also contain binders that can also adjust formulation texture and mouth feel.

The thickening agent can include the addition of polymers of acrylic acid crosslinked with an unsaturated polyfunctional agent such as a polyallyl ether of sucrose. These carboxy vinyl polymers have the CTFA (Cosmetic, Toiletry and Fragrance Association) adopted name of "carbomer." A carbomer can include negatively charged polyelectrolytes, such as Carbomer 956 (available from Lubrizol Corporation, Wickliffe, Ohio). The carbomer can be selected from the group consisting of acrylates/C10-30 alkyl acrylate crosspolymer, sodium polyacrylate; polyacrylate-1 Crosspolymer (available from Lubrizol); polyacrylate Crosspolymer-11 (available from Clariant, Inc., Louisville, Ky., USA), acrylates/C10-30 alkyl acrylate crosspolymer, and combinations thereof. The carbomer can be Carbomer 956. The composition can contain from about 0.1% to about 15% carbomer, from about 0.3% to about 10% carbomer, from about 0.5% to about 6% carbomer, from about 0.7% to about 3% carbomer, and/or in from about 0.9% to about 1.5% carbomer. Examples of additional carbomers can be found in U.S. Pat. No. 2,798,053.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Brookfield Viscosity Test

The viscometer is Brookfield viscometer, Model ½ RVT, with a Brookfield "Heliopath" stand (available from Brookfield Engineering Laboratories, Middleboro, Mass.). The spindle is a conventional "E-series" T-shaped spindle. The viscometer is placed on the Heliopath stand and leveled via spirit levels. The E spindle is attached, and the viscometer is set to 2.5 RPM while it is running. The viscosity is measured after 1 minute and the temperature is constant at 25° C. The "Brookfield Unit" in which results obtained from this method have traditionally been expressed is simply the direct readout of the instrument under standard conditions, i.e., using the "E" spindle at 2.5 RPM, or calculated equivalent.

pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

The pH of the liquid medication is measured using the calibrated pH meter at ambient temperature.

Phase Separation Method

After the toothpaste is made, 25 grams of the composition is placed in a polypropylene speed mix jar (max 40 SpeedMixer™ contain available from FlackTek™ Inc.) with a screwed lid screwed hand tight. Then, the container is placed in an oven (Espec™ LHV-113 Temperature and Humidity Cabinet was used here) at 40° C. for about 8 hours. Then, the container is removed and it is observed to see if any phase separation was visually perceptible.

EXAMPLES

|  | Ex. 1 (wt. %) | Ex. 2 (wt. %) | Ex. 3 (wt. %) | Ex. 4 (wt. %) | Ex. 5 (wt. %) | Ex. 6 (wt. %) |
| --- | --- | --- | --- | --- | --- | --- |
| Water | 20.26 | 20.26 | 20.26 | 10.68 | 22.52 | 11.19 |
| Lanette ® W[2] | 11.11 | 11.11 | 14.44 | 15.56 | 16.05 | 17.78 |
| Sorbitol Solution USP[3] | 30.57 | 37.01 | 29.23 | 30.04 | 32.48 | 29.96 |
| Saccharin Sodium USP Granular, High Moisture[4] | 0.45 | 0.45 | 0.45 | 0.45 | 0.50 | 0.45 |
| Potassium Nitrate USP | 5.00 | 5.00 | 5.00 | 5.00 | 5.56 | 5.00 |
| Sodium Fluoride | 0.24 | 0.24 | 0.24 | 0.24 | 0.27 | 0.24 |
| Sodium Acid Pyrophosphate | 0.11 | 0.11 | 0.11 | 0.09 | 0.12 | 0.12 |
| Sucralose | 0.25 | 0.25 | 0.25 | 0.25 | 0.28 | 0.25 |
| Zeodent ® 109[5] | — | 7.50 | — | — | — | — |
| Tospearl ® 145[6] | 10.00 | — | 10.00 | — | — | — |
| Zeodent ® 119[5] | — | — | — | 15.00 | — | 15.00 |
| Flavor | 2.15 | 2.15 | 2.15 | 2.15 | 2.39 | 2.15 |
| Sodium Lauryl Sulfate Solution (29%) | 20.00 | 17.86 | 17.86 | 20.00 | 19.84 | 17.85 |

[2]Lanette ® W is mixture (40:40:10) of cetyl alcohol/stearyl alcohol/sodium lauryl sulfate and is available from BASF Corp.
[3]Sorbitol Solution USP is an aqueous solution containing 70% sorbitol
[4]Saccharin Sodium USP Granular, high moisture contains up to 14% water
[5]Available from J. M. Huber Corporation, Edison, New Jersey
[6]Polymethyl organosiloxane particles, more specifically polymethyl organosiloxane silicone resin particles, available from Momentive ™ Performance Materials, New York Examples 1-6 were made as follows. A jacketed mix tank was set to 85° C. Water, sorbitol solution, and Lanette® W were added to the vessel with agitation until the temperature reached 80° C. and a solution that includes melted fatty alcohols and SLS was formed. Then, the heating jacket was reset to 25° C. and the batch was cooled. After the mixture cools, the following materials were added to the vessel: saccharin sodium, potassium nitrate, sodium fluoride, sodium acid pyrophosphate, and sucralose with agitation and homogenization. Next, the abrasive was added to the vessel with agitation and the mixture was thoroughly mixed. Once the abrasive had wetted out (i.e. no powders are floating on top of the liquid) the mixture was deaerated. Once the composition was approximately homogenous and approximately all of the air was removed, the flavor and remaining SLS were added to the vessel with agitation. The mixture was then deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Combinations

A. An oral care composition comprising: (a) a gel network phase comprising a fatty amphiphile and a secondary surfactant; (b) potassium nitrate; (c) from about 2% to about 25% abrasive, or from about 5% to about 20% abrasive, or from about 7% to about 18% abrasive, or from about 9% to about 16% abrasive; (d) and a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises at least about 12% fatty amphiphile, or at least 14% fatty amphiphile, or at least about 15% fatty amphiphile, or at least about 16% fatty amphiphile; and wherein phase separation is not visually perceptible as determined by the phase separation method.

B. An oral care composition comprising: (a) a gel network phase comprising a fatty amphiphile and a secondary surfactant; (b) potassium nitrate; (c) from about 2% to about 25% abrasive, or from about 5% to about 20% abrasive, or from about 7% to about 18% abrasive, or from about 9% to about 16% abrasive; (d) and a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises from about 10% to about 20% fatty amphiphile, or from about 12% to about 18% fatty amphiphile, or from about 14% to 17% fatty amphiphile; and wherein phase separation is not visually perceptible as determined by the phase separation method.

C. The oral care composition any one of the preceding paragraphs A-B wherein the abrasive comprises precipitated silica.

D. The oral care composition according to paragraph C wherein the precipitated silica has a BET surface area from about 19 $m^2/g$ to about 55 $m^2/g$.

E. The oral care composition according to paragraph A-D wherein the fatty amphiphile comprises a fatty alcohol selected from the group consisting of cetyl alcohol, stearyl alcohol, and combinations thereof.

F. The oral care composition according to any one of the preceding paragraphs A-E wherein the composition has a viscosity from about 5 BKUs to about 70 BKUs, or from about 10 BKUs to about 45 BKUs, or from about 15 BKUs to about 35 BKUs, or from about 18 BKUs to about 30 BKUs.

G. The composition according to any one of the preceding paragraphs A-F wherein the composition further comprises from about 15% to about 95% water, or from about 25% to about 70% water, or from about 30% to about 50% water, or from about 32% to about 45% water.

H. The composition according to any one of the preceding paragraphs A-G wherein the composition can contain from about 1% to about 15% secondary surfactant, or from about 2% to about 10% secondary surfactant, or from about 4% to about 8% secondary surfactant, or from 5% to about 7.5% secondary surfactant.

I. A method for making an oral care composition comprising the steps of: (a) combining water and a fatty amphiphile; (b) heating the water and the fatty amphiphile to about 80° C. until the fatty amphiphile melts and forms a solution; (c) cooling the solution; (d) adding a fluoride ion source and/or an abrasive and/or a peroxide; (c) adding secondary surfactant; (d) mixing until the composition is substantially homogeneous; (e) deaerating until the composition is substantially free of air; wherein a gel network is formed.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a. a gel network phase comprising a secondary surfactant and from about 15% to about 17%, by weight of the composition of a fatty amphiphile;
   b. from about 1% to about 8%, by weight of the composition, potassium nitrate;
   c. from about 2% to about 25%, by weight of the composition, abrasive; and
   d. a fluoride ion source selected from the group consisting of stannous fluoride, sodium fluoride, potassium fluoride, amine fluoride, sodium monofluorophosphate, indium fluoride, amine fluoride, and combinations thereof;
   wherein the fluoride ion source provides a fluoride ion concentration from about 0.005% to about 2.0%, by weight of the composition;
   and wherein phase separation is not visually perceptible as determined by a phase separation method.

2. The oral care composition of claim 1 wherein the abrasive comprises precipitated silica.

3. The oral care composition of claim 1 wherein the precipitated silica has a BET surface area from about 19 $m^2/g$ to about 55 $m^2/g$.

4. The oral care composition of claim 1 wherein the fatty amphiphile comprises a fatty alcohol selected from the group consisting of cetyl alcohol, stearyl alcohol, and combinations thereof.

5. The oral care composition according to claim 1 wherein the composition has a viscosity from about 5 BKUs to about 70 BKUs.

6. The composition of claim 1 wherein the composition further comprises from about 25% to about 70% water.

7. The composition of claim 1 wherein the composition contain from about 1% to about 4% secondary surfactant.

8. A method for making an oral care composition according to claim 1 comprising the steps of:
   a. combining water and a fatty amphiphile;
   b. heating the water and the fatty amphiphile until the fatty amphiphile melts and a solution is formed;
   c. cooling the solution;
   d. adding a fluoride ion source, an abrasive, potassium nitrate, and optionally a peroxide;
   e. adding a secondary surfactant;
   f. mixing until the composition is homogeneous; and
   g. deaerating until the composition is free of air; wherein a gel network is formed.

9. The method of claim 8 wherein the water and the fatty amphiphile is heated to about 80° C.

* * * * *